United States Patent [19]

Asano et al.

[11] 4,032,572

[45] * June 28, 1977

[54] METHOD FOR CONCENTRATING AN ACRYLAMIDE AQUEOUS SOLUTION

[75] Inventors: Shiro Asano, Yokohama; Kiyotaka Yoshimura, Mobara; Ryoji Tsuchiya, Kamakura; Tadatoshi Honda, Yokohama, all of Japan

[73] Assignee: Mitsui Toatsu Chemicals, Incorporated, Tokyo, Japan

[ * ] Notice: The portion of the term of this patent subsequent to Nov. 4, 1992, has been disclaimed.

[22] Filed: Dec. 3, 1975

[21] Appl. No.: 637,416

Related U.S. Application Data

[63] Continuation-in-part of Ser. No. 529,450, Dec. 4, 1974, abandoned, which is a continuation-in-part of Ser. No. 311,830, Dec. 4, 1972, Pat. No. 3,917,693.

[30] Foreign Application Priority Data

Dec. 6, 1971 Japan .............................. 46-97895

[52] U.S. Cl. .................. 260/561 N; 159/13 R; 159/13 A; 159/13 C; 159/48 L; 159/47 R; 159/49; 159/DIG. 10; 203/8; 203/9

[51] Int. Cl.$^2$ ..................................... C07C 103/08

[58] Field of Search ............................ 260/561 N

[56] References Cited

UNITED STATES PATENTS 3,917,693 11/1975 Asano et al. .................. 260/561 N Primary Examiner—Arthur P. Demers

[57] ABSTRACT

A method for economically concentrating an acrylamide aqueous solution by catalytic hydration without substantial deterioration in the product. According to the method, an acrylamide aqueous solution obtained from catalytic hydration, is concentrated by distillation while maintaining the solution in good contact with at least 0.1 mole. or more of air per mole of water distilled from the acrylamide aqueous solution.

8 Claims, 1 Drawing Figure

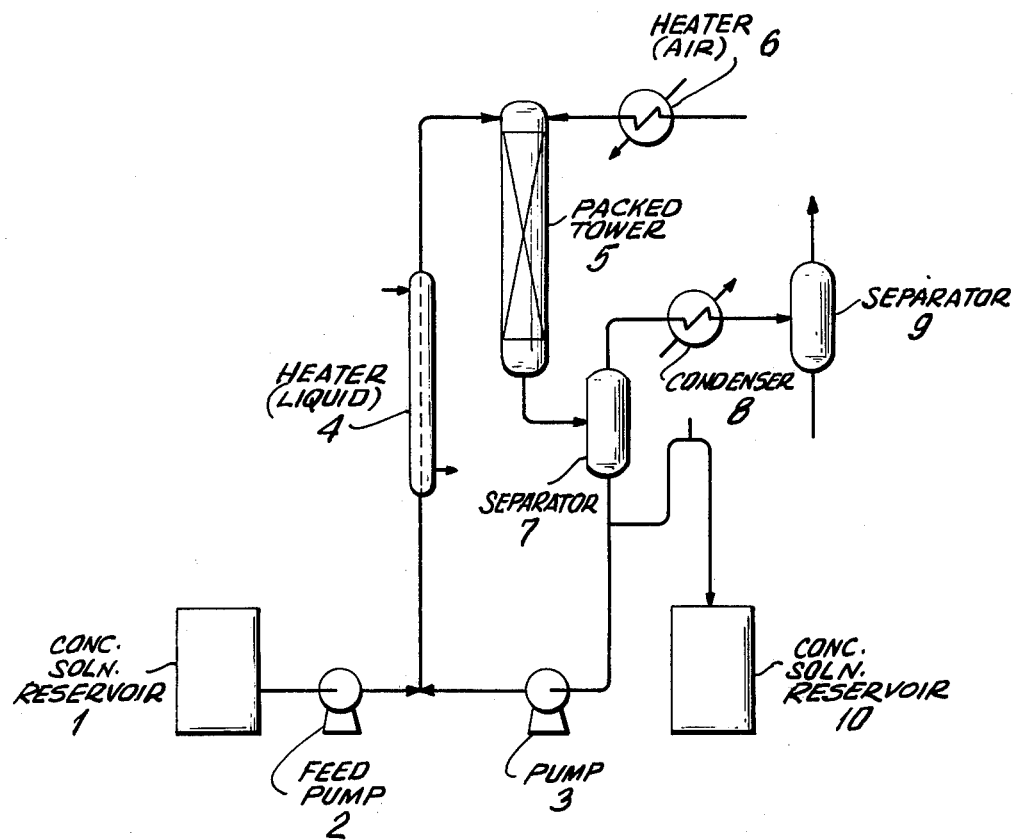

4,032,572

METHOD FOR CONCENTRATING AN ACRYLAMIDE AQUEOUS SOLUTION

FIELD OF THE INVENTION

The present invention relates to a process for concentrating an acrylamide aqueous solution obtained from catalytic hydration and producing acrylamide crystals of low acrylamide polymeric content. The present application is a continuation-in-part of Ser. No. 529,450 filed on Dec. 4, 1974 now abandoned, which is a continuation-in-part of Ser. No. 311,830 filed on Dec. 4, 1972, now Pat. No. 3,917,693, entitled "Method for Concentrating an Acrylamide Aqueous Solution", by the same inventors and assigned to Mitsui Toatsu Chemicals, Incorporated, a Japanese Corporation.

BACKGROUND OF THE INVENTION

Several processes have been reported heretofore for producing acrylamide by means of catalytic hydration. Typical of such processes are those disclosed in U.S. Pat. No. 3,381,034, in which a cuprous ion is employed; in U.S. Pat. No. 3,597,481, in which an oxide of silver, zinc or cadmium and an oxide of chromium are employed; in U.S. Pat. No. 3,631,104, in which copper oxide, copper-chromium oxide, copper-molybdenum oxide or a copper catalyst prepared by reducing any one of such oxides are employed; in U.S. Pat. No. 3,674,848, in which a I-B or II-B group metallic salt of acid cation exchange resin is employed; and in U.S. Pat. No. 3,673,250, in which a homogeneous catalyst consisting of organic phosphines or the like and transition metallic compounds are employed. Another example involves a process which is carried out by use of Raney copper, Ullmann copper, reduced copper or a catalyst made of substantially any one metal selected from a class including silver, gold and copper with a carrier (U.S. Pat. Application, Ser. No. 56,967, filed on July 21, 1970 and owned by the assignee of the present application). To date, however, no process suitable for industrial use is known for effectively concentrating an acrylamide aqueous solution by evaporating the water content while controlling the acrylamide polymer content in the acrylamide crystal or in the concentrated acrylamide aqueous solution product to less than 0.2 weight % in terms of butanol-insoluble residue.

In connection with the storage of such a vinyl monomer as liquid acrylic alkyl ester or the like, it is known that the vinyl monomer can be prevented from polymerizing by saturating it with air and/or oxygen. However, in a process wherein an acrylamide aqueous solution is concentrated by distillation at a high temperature, polymerization could occur more readily. Thus, it may be impossible to maintain the acrylamide polymer content in the resulting acrylamide crystals or concentrated acrylamide aqueous solution at a level less than 0.2 weight % merely by saturating the solution to be distilled with air and/or oxygen, or by applying the method of the conventional sulfuric acid process for producing acrylamide.

It may be clear to those skilled in the art that the technique for limiting the acrylamide polymer content to a level less than 2.0 weight % is extremely important when acrylamide crystals or an acrylamide-rich aqueous solution are used in the form of acrylamide monomer, for example, as a paper reinforcing agent.

OBJECTS OF THE INVENTION

The main object of this invention is, therefore, to provide an industrially acceptable process for producing an acrylamide crystal or an acrylamide-rich aqueous solution with only a small acrylamide polymer content.

Another object of this invention is to provide an improved and economical process for concentrating an acrylamide aqueous solution, which process can also be applied to an acrylamide aqueous solution having good polymerizability.

SUMMARY OF THE INVENTION

According to the process of this invention, the acrylamide polymer content in the acrylamide crystals or acrylamide-rich aqueous solution product can be controlled to be less than 0.2 weight % by distilling an acrylamide aqueous solution obtained from catalytic hydration while maintaining the acrylamide aqueous solution in contact with at least 0.1 mole. of air per mole. of water distilled. By maintaining the acrylamide aqueous solution in good contact with 0.1 to 30 moles of air, preferably 0.5 to 15 moles of air, per mole of water distilled, the concentration of an acrylamide aqueous solution becomes possible by distilling the aqueous solution at temperatures of from about 55° C to about 120° C under pressure ranging from about 200 to about 1470mm of mercury. As a result, the yield of the acrylamide crystals or acrylamide-rich aqueous solution can be increased quite economically.

BRIEF DESCRIPTION OF THE DRAWINGS

The accompanying FIG. 1 is a flow sheet representing a typical system which may be used for carrying out the process according to the present invention.

DETAILED DESCRIPTION OF THE INVENTION

Unlike an acrylamide aqueous solution prepared by the conventional sulfuric acid process for producing acrylamide, an acrylamide aqueous solution from catalytic hydration contains no significant by-product such as ammonium sulphate and no appreciable amounts of secondary reaction products, so that it may be purified by a simple purifying process into a monomer solution having a suitable adjustable concentration and a sufficient purity to be transferred to a subsequent polymerization process. To save in transportation costs or to improve the flexibility in the polymerization processing, the acrylamide aqueous solution may sometimes need to be further concentrated into a highly concentrated solution or into acrylamide crystals by crystallization or direct solidification of the highly concentrated acrylamide aqueous solution. A technically important problem which has to be solved in this connection is to inhibit the deterioration and especially the polymerization of acrylamide. For example, when it is preferred that the product contain no polymerization inhibitor or when the acrylamide is to be solidified directly from the concentrated solution, the acrylamide crystals and the acrylamide polymeric content in the concentrated acrylamide aqueous solution need to be controlled to less than 0.2 weight % in terms of butanol-insoluble residue.

With the conventional sulfuric acid process, the acrylamide and the by-product sulfate are separated from each other by crystallization. More specifically, in such a process the sulfate is usually first separated from a ternary system consisting of the acrylamide, a sulfate and water; then, acrylamide is separated by crystallization from the remaining solution which now contains only a small amount of residual sulfate. Thus the coexisting acrylamide polymer, polymerization inhibitor and other impurities, if any, are left behind in the mother liquor, so that the resulting acrylamide will contain only a limited amount of these materials. In this process, the polymerizability of acrylamide itself is also different from the usually encountered in the catalytic hydration with which this invention is concerned. Thus, one can readily understand why the concentration technique of the sulfuric acid process cannot be applied to the concentration of the acrylamide aqueous solution obtained from the catalytic hydration.

It may be also readily understood that a concentration process performed under reduced or limited pressure is to be preferred for concentrating an acrylamide aqueous solution while inhibiting polymerization and other deterioration in the product. However, it has been found that a considerably reduced pressure, for example 20mmHg, 30° C, must be attained in order to concentrate an acrylamide aqueous solution to 60% without using any polymerization inhibitor. This is not practical for any concentrating operation on an industrial scale, and it is almost impossible to further promote the concentration for solidification of the acrylamide.

It has now been discovered that, when a pure acrylamide aqueous solution is concentrated to dryness at room temperature and under reduced pressure, it is inevitable for a portion of the acrylamide dissolved in the solution to be polymerized; on the other hand, if the concentration process for an acrylamide aqueous solution is performed at temperatures of 55° to 120° C under reduced pressure of from about 200 to about 1470mmHg, while maintaining the solution in contact with a predetermined amount of air, fused acrylamide which contains almost no polymeric content may by obtained.

While it is known that oxygen or air act as a polymerization inhibitor for acrylamide, acrylic esters, or the like, it has been a common practice heretofore to remove the dissolved oxygen prior to polymerization. On the other hand, the process according to this invention possesses unique features and advantages as indicated in the following paragraphs:

1. In order to achieve a satisfactory polymerization inhibiting effect, it is necessary to maintain the acrylamide aqueous solution in good contact with air under agitation, for example, by using a greater amount of air than is commonly employed. As a result, the following two different effects can be achieved simultaneously and the polymerization inhibiting effect can be strikingly improved.

A. The use of a large amount of air results in a good contact between the solution and the air. Since the air also acts as a diluent for the water vapor generated, practically the same effect can be achieved as in a concentration process under reduced pressure. If air is added to the concentrated solution in an equimolar amount with the water vapor generated at a time when the concentrated solution has a concentration of 60%, the temperature of the concentrated solution will be 88° C, which is 17 degrees lower than the temperature that the concentrated solution might otherwise reach, if no air were employed. Consequently, the rate of polymerization of the acrylamide is repressed to a remarkable extent.

B. As the temperature falls, the solubility of the oxygen into an acrylamide aqueous solution increases. By using an increasingly larger amount of air, an increasingly higher partial pressure of the oxygen contained in the gaseous phase, i.e. a gaseous mixture of air and water vapor which are in contact with the acrylamide aqueous solution, will be obtained. This will lead to an increase in the amount of oxygen which is dissolved into the solution.

2. The polymerization inhibiting effect achieved permits the concentration of an acrylamide aqueous solution by distillation under pressures not greater than about 1470mmHg or slightly reduced pressures, for example, in the range between 760 and 200mmHg and at a relatively low temperature in the range of 120°–55° C. Thus, no expensive or complex apparatus is required for distillation under reduced pressure, and the ease in concentrating an acrylamide aqueous solution by distillation is considerable.

3. Fused acrylamide may be obtained by nearly completely evaporating the water content from the acrylamide aqueous solution. When cooled, the fused acrylamide may be crystallized. By applying the process of this invention to a highly purified aqueous solution which has been obtained from the catalytic hydration process, highly purified acrylamide crystals may be obtained directly from a crystallization process which is greatly simplified compared with any other commonly employed process.

Although acrylamide is a highly reactive compound and enters readily into polymerization, carbamyl ethylation or other amide group reactions, no secondary reaction occurs when an acrylamide aqueous solution is concentrated in accordance with the process of this invention, but crystals having a purity of 99.0% or above may readily be obtained when, for example, the solidified acrylamide is dried.

4. The process of this invention is most advantageous when it is applied to an acrylamide aqueous solution. The reason for this lies in that acrylamide is scarcely distilled due to its low vapor pressure and hence the recovery of water vapor by condensation is either unnecessary or it can be effected in a simple manner. In addition, the concentrator requires no fractionating section for separation of acrylamide from water. Thus, the process avoids any possible difficulty which may otherwise result from a relatively large amount of air passing through such a fractionating section.

It is known that such advantage is described above at (4) cannot be fully expected when an unreacted raw material such as acrylonitrile is present, or when a third component such as methanol is added for the purpose of improving solubility, or when the concentration process is applied to a vinyl polymerization type monomer having a low boiling point other than acrylamide, for example, an acrylic ester.

As noted above, when an acrylamide aqueous solution obtained from a catalytic hydration is to be concentrated by distillation, the solution first needs to be treated by means of a usual distillation process for removing acrylonitrile, if any.

The process of this invention may be carried out in the following four different manners; that is:

1. In the manner disclosed hereafter in Examples 1 to 5, in which an acrylamide aqueous solution is heated while bubbling air thereinto;

2. In the manner disclosed in Example 6, in which an acrylamide aqueous solution is sprayed into a flow of hot air to separate a concentrated solution for directly preparing acrylamide crystals;

3. In the manner disclosed in Example 7, in which an acrylamide aqueous solution is concentrated into a thin liquid film within an air flow; and 4. In the manner disclosed in Example 8 in which a preheated acrylamide aqueous solution is mixed with air and concentrated by distillation.

Of these four variants, two are more economically applicable to industrial purposes. They are specifically set forth in Example 4 (in which a double pipe concentrator is employed and an acrylamide aqueous solution is permitted to flow in parallel with air) and in Example 8 (in which an apparatus is employed with liquid heating section and a water evaporating section as shown in FIG. 1). With either one of the above-referred variants, the polymerization inhibiting effect can be achieved in the most simple manner. The so-called spray process, as illustrated in Example 6, is also useful for directly obtaining acrylamide crystals. Furthermore even a process for concentrating an acrylamide aqueous solution by distillation with use of a conventional packed tower may be employed.

The quantity of air feed may vary depending upon the variant process and the acrylamide concentration of the solution employed. At a concentration of less than 80%, 0.1 to 15 times as many moles. of air as there are moles. of distilled water may be employed. At higher concentrations, a larger quantity of air, for example 30 moles of air per mole. of distilled water, may be employed. Thus, the preferred air feed may be in the range of 0.5 to 15 moles. per mole. of water to be evaporated. When the moles of air are less than 0.1 times the number of moles of water to be evaporated, no such effect may be achieved; on the contrary, when the moles. of air exceed 30 times the moles. of water to be evaporated, satisfactory polymerization inhibiting effect may be achieved but, in such a case, excessively large and uneconomical equipment may be required.

As mentioned before, by supplying a large quantity of air to the distillation system, an acrylamide aqueous solution can be concentrated at a relatively high temperature of 100° to 120° C or so without accompanying formation of acrylamide polymer. However, when the concentration is carried out under reduced pressure, a pressure of at least 200 mmHg is normally required, because the oxygen dissolved in the acrylamide aqueous solution is reduced in quantity at a pressure of less than 150 mmHg. On the other hand, the concentration under a slightly increased pressure, for example above 760 to about 1470mmHg will incur no specific difficulty. In summary, the method for concentrating an acrylamide aqueous solution obtained from catalytic hydration is preferably carried out at 55° – 120° C under a pressure in the range of 200 to 760 mmHg while maintaining said solution in contact with 0.5 to 15 moles of air per mole of water being evaporated.

Examples of acrylamide aqueous solutions to which the process of this invention can be applied are the acrylamide aqueous solutions obtained from various catalytic hydration processes. These processes include those which employ such a catalysts as Raney copper, Ullmann copper, reduced copper, copper with a carrier, silver or gold; those where a cuprous ion or an oxide of silver, zinc, cadmium or chromium are used; those in which copper oxide, copper-chromium oxide, copper molybdenum oxide or a copper catalyst obtained by reducing any one of these oxides is used; those in which I-B or II-B group metallic salts of an acid cation exchange resin are used; and those in which a homogeneous catalyst composed of organic phosphines and transition metallic compounds is used. Similar effects may be obtained by applying the process of this invention to a neutralized mother liquor which is obtained by removing ammonium sulfate from a liquid resulting from the reaction according to the conventional sulfuric acid process for producing acrylamide, or by applying it to an aqueous solution having dissolved therein acrylamide crystals prepared by the sulfuric acid process.

Actually, there is no limitation in the concentration of the aqueous solution to be employed. Even an aqueous solution having an extremely low concentration may be concentrated into a so-called fused acrylamide which has a concentration of above 95%.

The presence of other solvents in the aqueous solution will have no adverse result; however, the advantages of this invention may sometimes fail to be fully achieved for that reason. Air may be used diluted with nitrogen or, conversely, added to oxygen to such an extend that it incurs substantially no danger.

The invention will now be described in greater details by way of examples. In the following examples, the results have been obtained in accordanced with standard definite analytical methods, which will be described. Concentration or purity of the acrylamide have been measured by bromometry. The measurement of pH was made by a usual pH meter. The color tone was measured by the so-called APHA method adapted for measuring the concentration of yellowish brown color in a liquid and such measurements were made for comparison purpose for solutions having an equal concentration of about 30%.

The butanol-insoluble residue was measured in the following manner; 7g of pure acrylamide was dissolved into 100 ml of butanol. The undissolved acrylamide was then separated by filtration and washed with a small amount of butanol. After drying at 100° C for 2 hours, the residual acrylamide was weighed. Most of the butanol-insoluble residue consisted of acrylamide polymer, but other components such as inorganic salts, if any, were also added in the measurement.

The determination of the salt content was made in the following manner: The sample solution (when the sample was in the form of crystal, it was dissolved in water to prepare an aqueous solution having a concentration of about 30%) was first treated with a cation exchange resin of the —$SO_3H$ type to liberate the acid, which was then titrated with caustic soda using bromothymol blue as an indicator. The value of the salt content normally represented the quantity of such salts as acrylic ammonium and the like, but the other inorganic salts, if any, were also added in the measurement.

EXAMPLE 1

75 parts by weight/hr of Raney copper catalyst and 785 parts by weight/hr of water are continuously supplied in the form of a slurry to a reactor containing 500 parts by wt. of Raney copper. At the same time, acrylonitrile was supplied to the reactor at a rate of 383 parts by wt. per hour. The mixture was retained within the reactor for 2.5 hours for reaction at 120° C. Then the reaction solution which contained almost no catalyst was removed from the top of the reactor, while a corresponding feed portion of the catalyst slurry was withdrawn at the bottom of the reactor. The composition of the liquid obtained by removing the catalyst from the reaction solution and the catalyst slurry was as follows:

Acrylonitrile 15 weight %
Acrylamide 20 weight %
Water 65 weight %
(conversion ratio, 50%)

Using a packed tower and a centrifugal membrane evaporator the liquid was then distilled under reduced pressure to prepare an acrylamide aqueous solution containing 30 weight % of acrylamide and 0.01 weight % of residual acrylonitrile.

Furthermore, acrylamide aqueous solution is treated with active carbon an amount of 1 part by weight as against 100 parts of aqueous solution, and active carbon is separated by means of filtration. And deionization is carried out using a column packed with a sulfonic acid type cation exchange resin by means of a dilute acid. Therefor, caustic soda is added to make its pH to nearly 6.5.

3,000g of such 30% acrylamide aqueous solution were then disposed in a flask provided with an agitator and immersed in a 110° C bath; the acrylamide aqueous solution was concentrated under normal pressure while bubbling air of ambient temperature at a rate of 570 l/hr. (normal condition). During the concentration, the temperature of the solution was about 85° C and the quantity of the distilled water was about 300 g/hr. In terms of moles., the air feed and the distilled water were 25.4 g-mole/hr. and 16.7 g-mole./hr. respectively; their molar ratio as 1.5.

After 5 hours, when the concentration of the solution appeared to have reached 60%, the concentration process was ceased. Then, the concentrated solution was analyzed together with the original unconcentrated solution. The results are set forth in the following table:

TABLE 1

|  | Original unconcentrated solution | Concentrated solution |
|---|---|---|
| Concentration of Acrylamide (%) | 31.5 | 60.6 |
| pH | 6.87 | 6.92 |
| Color Tone (APHA) (for 30% aqueous solution) | 10 | 15 |
| Butanol-Insoluble Residue (vs. acrylamide %) | not detected | 0.03 |
| Salt Content (milliequivalent/kg acrylamide) | 6.3 | 7.2 |

For purpose of comparison, 3,000g of an identical 30% aqueous solution were disposed in a flask immersed in a 110° C bath; and the solution was concentrated under reduced pressure of about 300 mmHg (absolute pressure) while bubbling air of ambient temperature into the solution through the tip of capillary at a rate of 20 l/hr (normal condition). During the concentration, the temperature of the aqueous solution was about 85° C and the quantity of the distilled water was about 400 g/hr. In terms of moles, the air feed and the distilled water were 0.9 g-mole./hr. and 22.2 g-mole./hr., respectively; their molar ratio was 0.04. After about 4 hours, when the concentration of the solution appeared to have reached about 60%, the concentration process was ceased and the concentrated solution was analyzed. The results were as follows:

Concentration of Acrylamide (%) 59.0
pH 7.05
Color Tone (APHA) (for 30% aqueous solution); 20
Butanol-Insoluble Residue (vs. acrylamide %); 0.27

It will be seen from the preceding that the polymer content in the concentrated solution is relatively increased.

EXAMPLE 2

An experiment similar to that disclosed in Example 1 was performed under a reduced pressure of 230 mmHg. During the concentration, the temperature of the acrylamide aqueous solution was about 60° C and the quantity of the water distilled was about 600 g/hr. In terms of moles, the air feed and the distilled water were 25.4 g-mole./hr. and 33.3 g-mole./hr., respectively; their molar ratio was 0.76. After 2 hours, when a concentration of about 60% appeared to have been reached, the concentration process was ceased and the concentrated solution was analyzed. The results were as follows:

Concentration of Acrylamide (%) 62.1
pH 6.8
Color Tone (APHA) (for 30% aqueous solution); 10
Butanol-Insoluble Residue (vs. acrylamide %); 0.05
Salt Content (milliequivalent/kg acrylamide); 6.5

Almost no deterioration was observed in the concentrated solution except that the butanol-insoluble residue was increased slightly compared with the original aqueous solution.

EXAMPLE 3

300g of a 30% aqueous solution identical to that used in Example 1 were disposed in a flask having an agitator and immersed in a 100° C bath and the concentration was carried out at normal temperature while bubbling air of ambient temperature at a rate of 600 l/hr. (normal condition). The temperature of the acrylamide aqueous solution was about 80° C at an early stage of the concentration process, and then the temperature of the solution rose gradually until it reached about 95° C after 100 minutes, when the evaporation of water was scarcely observed. The distilled water was 210g in total. The rate of the water, although it was gradually lowered as the process proceeded, was 126 g/hr. in average. Thus, in terms of moles., the air supplied and the water distilled were 26.8g-mole./hr. and 9.5 g-mole./hr., respectively; their molar ratio was 2.8. Under continuous agitation and air supply, the concentrated solution was cooled for solidification. The butanol-insoluble residue of solidified acrylamide was 0.03%, and the color tone (ALPHA) of the 30% acrylamide aqueous solution prepared by dissolving the resulted acrylamide in water was 20.

For purpose of comparison, 100g of an identical 30% aqueous solution were disposed in a flask immersed in a 30° C bath and the concentration was carried out under a reduced pressure of 10 mmHg (absolute pressure). After about 15 minutes, when crystallization was observed, the concentration process was ceased and the pasty content consisting of a crystallized and viscous polymer was taken out of the flask. Identical experiments were repeated only to attain the same result. Similar results were obtained from an identical experiment which was conducted by using a 30% aqueous solution prepared by dissolving in water a commercially available crystallized acrylamide prepared by the sulfuric acid process.

EXAMPLE 4

At the bottom of the inner pipe of a double pipe concentrator (the concentrator including a 1-inch SUS-27 steel pipe and a 2-inch SUS-27 steel pipe), 540 1/hr. of air (normal STP condition) and 2,120 g/hr. of 38% acrylamide aqueous solution prepared as described in Example 1 were supplied into the concentrator, while permitting 1,470 g/hr. of concentrated solution, 740 g/hr. of distilled water and air to flow out of the concentrator at the top of the inner pipe. While supplying water vapor as a heat source through the outer pipe at a normal pressure, the concentration was carried out at about 95° C under a normal pressure. In such a process, the residence time of the solution in the concentrator seemed to be about 10 minutes. (The above-described concentration process will simply be expressed hereunder as the first-stage concentration).

Subsequently, 1,440 g/hr. of the concentrated solution resulted from the first-stage concentration and 1,350 1/hr. of air (normal STP condition) were supplied into the same concentrator to carry out another concentration at about 92° C under ambient pressure. As a result, 840 g/hr. of further concentrated solution and 600 g/hr. of distilled water were obtained. (Such a concentration process will simply be called hereunder as the second-stage concentration). In order to prevent crystallization, the concentrated solution resulted from the second-stage concentration was placed in a reservoir maintained at 60° C. This reserve solution was then poured into SUS-27 steel dishes at an interval of 20 minutes to let the solution solidify into flake-like solids by air-cooling. Using a rotary dryer, the resulted flakes were dried for 2 hours at 60° C to yield dried crystals. In the first- and second-stage concentrations, the moles. of the air feed and the distilled water were as set forth in the following table:

TABLE II

|  | First-Stage Concentration | | Second-Stage Concentration | |
|---|---|---|---|---|
|  | Air Feed | Distilled Water | Air Feed | Distilled Water |
| Flow Rate in Moles. (g-mole./hr.) | 24.0 | 41.0 | 60.3 | 33.3 |
| Molar Ratio | 0.6 | | 1.8 | |

With respect to the liquids and solids obtained from each stage of concentration, the analytical results were as follows:

TABLE III

|  | Original Solution | Concentrated Solution from first-stage concentration | Flake Material | Dried Crystal |
|---|---|---|---|---|
| Concentration or Purity of Acrylamide (%) | 38.0 | 57.8 | 92.1 | 98.6 |
| Water Content (%) | — | — | 6.9 | 0.3 |
| Color Tone (APHA) (for 30% aqueous solution) | 8 | 10 | 10 | 10 |
| Butanol-Insoluble Residue (vs. acrylamide %) | not detected | 0.01 | 0.02 | 0.04 |
| Salt Content (milliequivalent/kg acrylamide) | 11.5 | — | — | 14.3 |

It will now be clear to those skilled in the art that as the concentration and drying operations proceed, the values of color tone, butanol-insoluble residue and salt content are increased slightly but not to such an extent as to reduce the value of the resulted product as a commodity.

50g of dried crystals were then dissolved in 450g of water within a flask having an agitator and immersed in a 40° C bath. Dissolved oxygen was removed by bubbling nitrogen into the solution. When the temperature of the solution reached 40° C, 2 ml. of 15% ammonium persulfate aqueous solution and 4 ml. of 1% sodium hydrosulfite aqueous solution were added simultaneously under agitation. After an induction period of 60 seconds, when the temperature rise indicative of the initiation of polymerization was observed, the agitation was ceased temporarily. After that, when the temperature began to fall, agitation was resumed and continued for another 2 hours. The viscosity of the resulted solution at a temperature of 25° C was 102 poise (Brookfield Viscometer).

An identical polymerization reaction was carried out with a 10% aqueous solution prepared from the same original solution. In this case, the induction period was 70 seconds and the viscosity of the polymerized solution was 110 poise. This shows that almost no product deterioration resulted from the concentration and crystallization operations.

After about two days of operation, an inspection of the interior of the concentrator was made. No deposition of polymers was found on the heat-transfer surface or any other surface areas. This means that no diffculty will be encountered during a long period of operation.

EXAMPLE 5

An experiment similar to the first-stage concentration disclosed in Example 4 was carried out with reduced air feed of 130 1/hr. (normal STP condition) and by using water vapor controlled in such a manner that the resulting solution had a concentration similar to that of the solution obtained from Example 4. As a result, the temperature of the solution in the concentrator reached 102° C, and 700g of distilled water and 1,430g of 56% concentrated solution were obtained per hour. In this experiment, the air feed and the distilled water were, in terms of moles. 5.8 g-mole./hr. and 38.9 g-mole./hr., respectively; their molar ratio was 0.15.

The butanol-insoluble residue contained in the concentrated solution was 0.14% (vs. acrylamide %). Although this percentage is slightly higher than 0.01% (vs. acrylamide %) as for the solution from the first-stage concentration of Example 4, its quantity is so insignificant as to incur substantially no practical disadvantage.

EXAMPLE 6

An experiment was made using a spray dryer provided with a cylindrical container body 2m in diameter and 2.5m high, and so constructed as to have a conical bottom and a spray means mounted on top. A 60% concentrated acrylamide aqueous solution obtained from the first-stage concentration in Example 4 was supplied into the spray dryer at ambient temperature at a rate of 12 1/hr. and sprayed. At the same time, 120° C air was supplied into the spray dryer at the top thereof at a rate of 10 m³/min., while discharging crystallized acrylamide together with air (cooled to 65° C)

from the bottom of the spray dryer. Discharged acrylamide crystals were collected in a bag filter.

The water content and the butanol-insoluble residue were 0.7% and 0.03%, respectively.

In this experiment, the distilled water was about 7 kg/hr. The distilled water and air feed were, in terms of moles., 0.39 g-mole./hr. and 0.45 g-mole./hr, respectively; their molar ratio was 1.1.

EXAMPLE 7

A double pipe assembly 0.8m long and consisting of a SUS-27 steep pipe of 1-inch diameter and a SUS-27 steel pipe of 2-inch diameter was employed as a wetted-wall concentrator. Water vapor was introduced into the outer pipe as a heat source at ambient temperature; air was supplied into the inner pipe at the bottom thereof at a rate of 550 l/hr. (normal STP condition), and a 30% aqueous solution as in Example 1 was supplied into the inner pipe at the top thereof so that if flowed down along the inner wall surface of the inner pipe in the form of a uniform liquid film. The distilled water was discharged from the top of the concentrator at a rate of 240 g/hr. together with air, while the concentrated solution was collected at a rate of 430 g/hr. at the bottom of the concentrator. In terms of moles., the air feed and the distilled water were 24.5 g-mole./hr. and 13.3 g-mole./hr., respectively; their molar ratio was 1.8. The concentration of the resulting solution was measured to be 48%, the butanol-insoluble residue could not be detected as it was the case in the original 30% aqueous solution.

EXAMPLE 8

A concentration as in Example 4 was carried out using a second-stage concentrator, an apparatus provided with a liquid-heating section and a water evaporating section as shown schematically in FIG. 1. A liquid heater 4 comprises a jacket encircling a ½-inch SUS-27 steel pipe to define an annular space between the jacket and the pipe, so that steam can be supplied into the space at ambient temperature. A packed tower 5 comprises a 2-inch diameter, 80cm long SUS steel pipe, in which porcelain ⅜ inch Raschig rings are placed.

An aqueous solution obtained from the process of Example 4 was first disposed in a first-stage concentrated solution reservoir 1. By use of a feed pump 2, the solution was forced into the packed tower 5 after passing through the liquid heater 4 at a rate of 1,370 g/hr. Air which had been preheated to 100° C by means of an air-heater 6 was supplied simultaneously into the packed tower 5 at a rate of 5.1 N m³/hr. Both air and solution were brought into good contact with each other while flowing down within the packed tower 5, so that a concentrated solution having a temperature of about 65° C and air containing some water were obtained in the packed tower 5. The concentrated solution and the air were then introduced into a first liquid-gas separator 7 and separated therein from each other. The air having water therein was then forced to pass through a condenser 8 to thereby separate the water from the air. The concentrated solution, on the other hand, was heated in the liquid heater 4 to 80° C together with the solution coming from the feed pump 2 at a rate of 12.5 kg/hr., and returned to the packed tower 5 by means of a pump 3. At the same time, a portion of the concentrated solution was continuously removed to a second concentrated solution reservoir 10 which was maintained at 60° C. The concentration of such a solution was 90 – 92%.

In terms of moles., the air feed and the distilled water were 228 g-mole./hr. and 250 g-mole./hr., respectively, their molar ratio was 0.91.

As in Example 4, the concentrated solution was dried into flakes and then into dry crystals. The following table represents in comparison the analytical results of the original solution, the concentrated solution from the first-stage concentration, the flakes and the dry crystals.

TABLE V

| | original Solution | Concentrated Solution from first-stage concentration | Flakes | Dry crystals |
|---|---|---|---|---|
| Concentration or Purity of Acrylamide (%) | 30.5 | 60–62 | 90–92 | 98.8 |
| Water Content (%) | — | — | — | 0.4 |
| Color Tone (APHA) (for 30% aqueous solution) | 5 | 5–10 | 5–10 | 10 |
| Butanol-Insoluble Residue (vs. Acrylamide (%) | not detected | 0.01 | 0.01 | 0.02 |

In this experiment, the color tone and the butanol-insoluble residue were increased slightly as the concentration or drying operations proceeded, but not to such an extent as to reduce the value of the final product as a commodity.

After continuing such a concentration operation for 7 days, an insepction was made of the interior of the apparatus. No deposition was found either in the liquid-heating section or in the packed tower 5. This means that the illustrated apparatus is capable of withstanding a continuous operation for an extended period of time.

EXAMPLE 9

Tests were carried out for the acrylamide aqueous solutions prepared by various catalytic hydration processes. In the cases where it was required to do so, each solution was tested after removal of unreacted acrylonitrile residue contained therein. Each of the sample solutions was prepared by a definite catalytic hydration process, as described herebelow.

SAMPLE 1

In a 30mm diameter and 300mm long reaction tube were charged 390g (or 220ml in volume) of cupric oxide pellets (manufactured by Nikki Chemical Company Ltd.). The pellets were then reduced at 200°–270° C with hydrogen gas and nitrogen gas passing through the reaction tube at a rate of 200 ml/min. and 400 ml/min., respectively, to thereby prepare a reduced copper catalyst. From the reduction in weight of the pellets, it was found that the reduction ratio of the resulted catalyst was 98%. Then, acrylonitrile and water were continuously supplied to the reaction tube at a rate of 140 g/hr. and 690 g/hr., respectively to carry out reaction at 120° C. The reaction solution was force-circulated within the reaction tube at a rate of 40 l/hr. to thereby promote the preparation of an acrylamide aqueous solution. The conversion ratio of acrylonitrile into acrylamide was 70%.

SAMPLE 2

A reduced copper-chromium catalyst was prepared by a reducing operation which was similar to that employed for preparing the reduced copper catalyst except that 470g of copper-chromium pellets (manufactured by Nikki Chemical Co., Ltd.) were used. Then, using such a reduced copper-chromium catalyst, a catalytic hydration was conducted under conditions of Sample 1. Accordingly, an aqueous solution of acrylamide was prepared at an almost equal conversion ratio.

SAMPLE 3

In a 1 reaction tank (made of SUS-27 stainless steel) provided with a catalyst separator and an agitator, were disposed 250g of copper powder. Then, acrylonitrile and water (dissolving therein 1/69 parts by weight of cupric chloride) were continuously supplied to the reaction tank at a rate of 140 g/hr. and 690 g/hr. respectively and reacted at 120° C. The conversion ratio of acrylonitrile to acrylamide was 14%.

SAMPLE 4

In the reaction tank of Sample 4, were disposed 250g of a heterogeneous catalyst consisting of 90 weight % silver oxide and 10 weight % chromium oxide. Then, acrylonitrile and water were continuously supplied to the reaction tank at a rate of 140 g/hr. and 690 g/hr. respectively and reacted at 120° C. The conversion ratio was 32%.

SAMPLE 5

Zinc resinate was prepared by treating a commercially available sodium type amberlite IRC-50 (registered trademark) with 5% zinc chloride aqueous solution. In the same reaction tank as in Sample 3, 200g of acrylonitrile, 300g of water and 100g of zinc resinate were reacted for 4 hours at 120° C, in the presence of a small quantity of an oxidation inhibitor. The conversion ratio of acrylonitrile to acrylamide was 11%.

The acrylamide aqueous solutions prepared from the above-described various processes were purified in accordance with the process of Example 1, and concentrated in accordance with the process of Example 2. The results of such concentration operations were as follows:

TABLE VI

| Sample No. | Catalyst Used | Concentration before Concentrated (weight %) | Concentration after Concentrated (weight %) | Butanol-Insoluble Residue (weight %) |
|---|---|---|---|---|
| 1 | Reduced Copper | 30 | 65 | 0.05 |
| 2 | Reduced Copper-Chromium | 30 | 65 | 0.08 |
| 3 | Copper Powder+ Cupric Chloride | 30 | 55 | 0.15 |
| 4 | silver Oxide+ Chromium Oxide | 30 | 55 | 0.19 |
| 5 | Zinc Resinate | 30 | 55 | 0.13 |

As far as pH, color tone, butanol-insoluble residue and salt content are concerned, the relationship between each of the acrylamide concentrated aqueous solutions and each corresponding unconcentrated acrylamide aqueous solution was found to be almost equal to that in the acrylamide aqueous solution prepared by using a Raney copper catalyst.

EXAMPLE 10

At the bottom of the inner pipe of a double pipe concentrator, 120 l/hr. of air and 3100 g/hr. of 20% acrylamide aqueous solution prepared as described in Example 1 were supplied into the concentrator, while supplying water vapor as a heat source through the outer pipe of the concentrator at a pressure of 1.5 kg/cm$^2$G (1860mmHg). The concentrated acrylamide aqueous solution flown out the inner pipe was introduced and collected in a tank, while permitting a mixed gas consisting of air and water vapor to be introduced into a water-cooled condenser. The condensed water was collected and the air was discharged out through a discharge valve which was a control valve used for the purpose of adjusting the pressure in the concentrator to 1 kg/cm$^2$G (1470mmHg). As a result, the acrylamide aqueous solution was concentrated to about 29% and an amount of butanol-isoluble residue was found to be 0.3% based on the concentrated acrylamide solution. The temperature of the concentrated acrylamide solution flown out of the concentrator was about 118° C and 950 g/hr of distilled water was obtained. Molar ratio of air feed to distilled water was calculated to be 0.1 : 1. These conditions and results were summarized in Experiment 1 of Table VII shown below.

Experiments 2–8 were conducted in the same manner as described above varying experimental conditions. The results were also shown in Table VII.

Table VII

| Experiment No. Condition | 1 | 2 | 3 | 4 | 5 | 6 | 7 | 8 |
|---|---|---|---|---|---|---|---|---|
| Concentration of Acrylamide Solution Supplied (%) | 20 | 20 | 20 | 20 | 20 | 20 | 20 | 20 |
| Amount of Acrylamide Solution Supplied (g/hr) | 3100 | 850 | 2200 | 1400 | 610 | 3100 | 2200 | 2200 |
| Pressure Inside the Concentrator (mmHg) | 1470 | 1470 | 200 | 400 | 200 | 1350 | 110 | 200 |
| Pressure of the Water Vapor * (mmHg) | 1860 | 1860 | 300 | 900 | 300 | 1860 | 150 | 300 |
| Volume of Air Feed (l/hr) | 120 | 25000 | 700 | 2000 | 18000 | 0 | 0 | 0 |
| Result | | | | | | | | |

Table VII-continued

| Experiment No.<br>Condition | 1 | 2 | 3 | 4 | 5 | 6 | 7 | 8 |
|---|---|---|---|---|---|---|---|---|
| Concentration of Acrylamide Solution Obtained (%) | 29 | 98 | 30 | 90 | 98 | ** | 28 | 28 |
| Temperature of Acrylamide Solution (° C) | 118 | 120 | 55 | 89 | 58 | 118 | 55 | 68 |
| Amount of Distilled Water Collected (g/hr) | 950 | 630 | 650 | 1090 | 430 | | 600 | 640 |
| Molar Ratio (Air Feed/Distilled Water) | 0.1 | 30 | 0.9 | 1.5 | 30 | | 0 | 0 |
| Butanol-Insoluble Residue (%) | 0.3 | 0.5 | 0.1 | 0.0 | 0.0 | | 2.3 | 2.8 |

\* Pressure inside the outer pipe of the concentrator.
\*\* The concentrator and discharge end thereof were soon clogged by viscous polymerized acrylamide solution and the further operation could be no more continued.

What is claimed is:

1. Method for concentrating acrylamide aqueous solutions obtained from catalytic hydration comprising concentrating the acrylamide aqueous solution by evaporating the water content thereof while maintaining the said solution on contact with from 0.1 to 30 moles of air per mole of water being evaporated at a temperature of between 55° and 120° C and a pressure of between 200 and 1470 mmHg.

2. Method according to claim 1, wherein the acrylamide aqueous solution is concentrated while maintaining the solution in contact with 0.5 to 15 moles. of air per mole. of water being evaporated.

3. Method according to claim 1, wherein the acrylamide aqueous solution is concentrated after removal of unreacted acrylonitrile residue contained therein.

4. Method according to claim 3, wherein said catalyst hydration employs a catalyst selected from the group consisting of Raney copper, Ulmann copper, reduced copper, reduced copper-chromium, copper powder-cupric chloride, silver oxide-chromium oxide, and zinc salts of acid cation exchange resins.

5. Method for concentrating an acrylamide aqueous solution according to claim 1, wherein said acrylamide aqueous solution is concentrated at 55° to 120° C under a pressure in the range of 200 to 760 mmHg while maintaining said solution in contact with 0.5 to 15 moles. of air per mole. of water being evaporated.

6. The method according to claim 1, wherein the acrylamide aqueous solution is sprayed into a flow of hot air to separate a concentrated solution for obtaining acrylamide crystals.

7. The method according to claim 1, wherein the acrylamide aqueous solution is concentrated into a thin liquid film within an air flow.

8. The method according to claim 1, wherein the acrylamide aqueous solution is first preheated, then mixed with air and, finally, concentrated by evaporation.

* * * * *